(12) United States Patent
Burbank et al.

(10) Patent No.: US 6,312,429 B1
(45) Date of Patent: *Nov. 6, 2001

(54) ELECTROSURGICAL LESION LOCATION DEVICE

(75) Inventors: Fred H. Burbank, San Juan Capistrano; Frank R. Louw, Carlsbad; Paul Lubock, Laguna Niquel; Richard L. Quick, Trabuco Canyon, all of CA (US)

(73) Assignee: Senorx, Inc., Irvine, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/356,187

(22) Filed: Jul. 16, 1999

Related U.S. Application Data

(63) Continuation-in-part of application No. 09/146,185, filed on Sep. 1, 1998.

(51) Int. Cl.$^7$ ..................................................... A61B 18/18
(52) U.S. Cl. ................................ 606/47; 606/41; 606/48; 607/101
(58) Field of Search ................................ 606/41, 45, 47, 606/48, 49, 50, 13–16; 607/100, 101, 105, 113, 106, 122

(56) References Cited

U.S. PATENT DOCUMENTS

Re. 33,925 * 5/1992 Bates et al. .............................. 606/48

(List continued on next page.)

FOREIGN PATENT DOCUMENTS

98/084441   3/1990 (WO).

(List continued on next page.)

OTHER PUBLICATIONS

Stereotactic Breast Biopsy: Its History, Its Present, and Its Future, F. Burbank, M.D., *The American Surgeon*, Feb. 1996, vol. 62, pp. 128–150.

(List continued on next page.)

*Primary Examiner*—Linda C. M. Dvorak
*Assistant Examiner*—R. Kearney
(74) *Attorney, Agent, or Firm*—Heller Ehrman White & McAuliffe, LLP

(57) ABSTRACT

A device for localizing a target tissue mass in a body includes a tubular trocar portion having a distal end and a proximal end portion that is removably attachable to a handle portion. The trocar portion contains at least a first plurality of locator wires that are movable between a retracted position within the trocar and a deployed position extending radially from the trocar. In a preferred embodiment, the trocar portion has an electrosurgical cutting element at its distal end, and first and second pluralities of locator wires that, when deployed, respectively define first and second locating perimeters. The first plurality of locator wires is connected to a first wire carrying member longitudinally mounted for axial movement within the trocar portion between a proximal position corresponding to the retracted position of the first plurality of locator wires, and a distal position corresponding to the deployed position of the first plurality of locator wires. The second plurality of locator wires is connected to a second wire-carrying member longitudinally mounted in the trocar portion, coaxially with the first tubular member, for movement between a distal position corresponding to the retracted position of the second plurality of locator wires, and a proximal position corresponding to the deployed position of the second plurality of locator wires. The trocar portion has an intermediate portion having first and second pluralities of slot-shaped apertures through which the first and second pluralities of locator wires emerge when moved to their respective deployed positions. With the locator wires in their retracted position, the trocar is passed through a target tissue mass until the intermediate portion is within the mass. The locator wires are then deployed within the mass to anchor the trocar therein and to mark the site for a surgical procedure. In the preferred embodiment, the locator wires are electrically energized to facilitate their deployment electrosurgically.

43 Claims, 11 Drawing Sheets

U.S. PATENT DOCUMENTS

| | | |
|---|---|---|
| 33,925 | 5/1992 | Bales et al. . |
| Re. 34,056 | 9/1992 | Lindgren et al. ............... 128/754 |
| 4,362,160 | 12/1982 | Hiltebrandt . |
| 5,047,027 | 9/1991 | Rydell ............................ 606/48 |
| 5,064,424 | 11/1991 | Bitrolf ............................ 606/46 |
| 5,133,359 | 7/1992 | Koedem ......................... 128/754 |
| 5,324,288 | 6/1994 | Billings et al. ................. 606/45 |
| 5,415,656 | 5/1995 | Tihon et al. .................... 606/46 |
| 5,526,822 | 6/1996 | Burbank et al. ................ 128/754 |
| 5,649,547 | 7/1997 | Ritchart et al. ................. 128/754 |
| 5,683,384 | 11/1997 | Gough et al. . |
| 5,735,847 * | 4/1998 | Gough et al. ................... 606/41 |
| 5,752,972 * | 5/1998 | Hoogeboom .................... 606/205 |
| 5,795,308 | 8/1998 | Russin . |
| 5,810,806 | 9/1998 | Ritchart et al. . |
| 5,868,740 | 2/1999 | LeVeen et al. . |

FOREIGN PATENT DOCUMENTS

| | | |
|---|---|---|
| WO 97/29702A1 | 8/1997 | (WO) . |
| 98/08441 | 3/1998 | (WO) ..................... A61B/10/00 |

OTHER PUBLICATIONS

Percutaneous Biopsy Techniques, Timothy J. Micklos, *Manual of Oncologic Therapeutics* (1989/1990), pp. 39–42.

Coaxial Core Needle Biopsy Under Mammogrphic Guidance: Indications and Applications, Whitman et al., AJR:171 Jul. 1998, pp. 67–70.

* cited by examiner

ELECTROSURGICAL LESION LOCATION DEVICE

CROSS-REFERENCE TO RELATED APPLICATIONS

This application is a continuation-in-part of co-pending U.S. patent application Ser. No. 09/146,185, filed Sep. 1, 1998 by Burbank et al., incorporated by reference herein in its entirety.

FEDERALLY-FUNDED RESEARCH OR DEVELOPMENT

Not Applicable

BACKGROUND OF THE INVENTION

The present invention relates generally to the field of electrosurgical instruments. More specifically, it relates to a device that electrosurgically fixes and identifies the location, in situ, of a pathologically suspect tissue mass in a patient's body, for facilitating the accurate surgical removal of the mass.

It is often medically desirable to remove a pathologically suspect tissue mass, such as a suspected tumor or lesion, from a patient's body. For example, in treating breast cancer, a suspicious tissue mass is typically identified and localized by imaging means, such as mammography or ultrasound. Once localized, the mass is typically subjected to a biopsy to determine whether or not it is malignant. Often, the biopsy will be an "open" biopsy, in which all or part of the identified mass is surgically removed, sometimes with a surrounding margin of tissue.

The identification and localization of the suspect mass is usually performed by a radiologist. The patient is then typically transported to an operating room for surgery. To allow the surgeon to be able to locate the identified mass, the radiologist places one or more localization wires or "Kopan's" wires into the breast to define and locate the tissue mass to be removed. In using a localization wire, a hollow needle or cannula, containing the localization wire, is inserted into the breast under local anaesthesia, while the breast is under compression during the imaging procedure, until the distal end of the localization wire passes through the suspect mass. The localization wire is anchored distally beyond the mass by means such as a barb or hook at the distal end of the wire. The cannula is then removed from the body, leaving the wire in place and extending from the body as a marker for the surgeon.

The above-described procedure has certain shortcomings, however. One problem stems from the fact that the localization wire is inserted while the breast is under compression during mammography. When the breast is released from compression, the distal end of the wire often migrates and thus shifts position with respect to the targeted tissue mass. This may lead to inaccurate placement of the incision for the biopsy, with the result that either an excess of tissue outside of the target tissue mass is removed, or less than all of the target tissue mass is removed. In addition, the wire is sometimes inadvertently shifted, severed, or pulled out during surgery, thereby defeating its purpose of accurately guiding the surgeon to the target tissue mass. Any inaccuracies in guiding the surgeon can result in larger than necessary amounts of healthy tissue being removed, with resultant deformation and scarring of the breast, or in the need to re-enter the incision site to remove parts of the target tissue mass that were missed on the first biopsy attempt.

Another shortcoming associated with prior art localization devices is that, while the location of the target tissue mass can be marked, no indication is provided of the dimensions of the mass. Thus, accurate removal of the desired amount of tissue depends on the surgeon's ability to determine the boundaries of the tissue mass during surgery.

It would therefore be advantageous to provide a localization device that minimizes or eliminates the aforementioned problems associated with the migration and inadvertent removal of the localization wire. It would be further advantageous for such a device to provide an accurate indication of the dimensions and boundaries of the target tissue mass. Furthermore, such a device should be easy to use, and should be compatible with existing imaging equipment and surgical methods.

SUMMARY OF THE INVENTION

Broadly, the present invention is a device for localizing a target tissue mass in a body, comprising a tubular trocar with at least a first plurality of locator wires that are movable between a retracted position fully contained within the trocar and a deployed position extending radially from the trocar. In a preferred embodiment, the device includes an electrosurgical cutting element at its distal end, and first and second pluralities of locator wires that, when deployed, respectively define first and second locating perimeters. The first plurality of locator wires is connected to a first tubular wire-carrying member longitudinally mounted for axial movement within the trocar between a proximal position corresponding to the retracted position of the first plurality of locator wires, and a distal position corresponding to the deployed position of the first plurality of locator wires. The second plurality of locator wires is connected to a second tubular wire-carrying member longitudinally mounted in the trocar, coaxially with the first tubular member, for movement between a distal position corresponding to the retracted position of the second plurality of locator wires, and a proximal position corresponding to the deployed position of the second plurality of locator wires. The trocar has a portion having first and second pluralities of slot-shaped apertures through which the first and second pluralities of locator wires emerge when moved to their respective deployed positions.

DETAILED DESCRIPTION OF A PREFERRED EMBODIMENT

Figure 1:
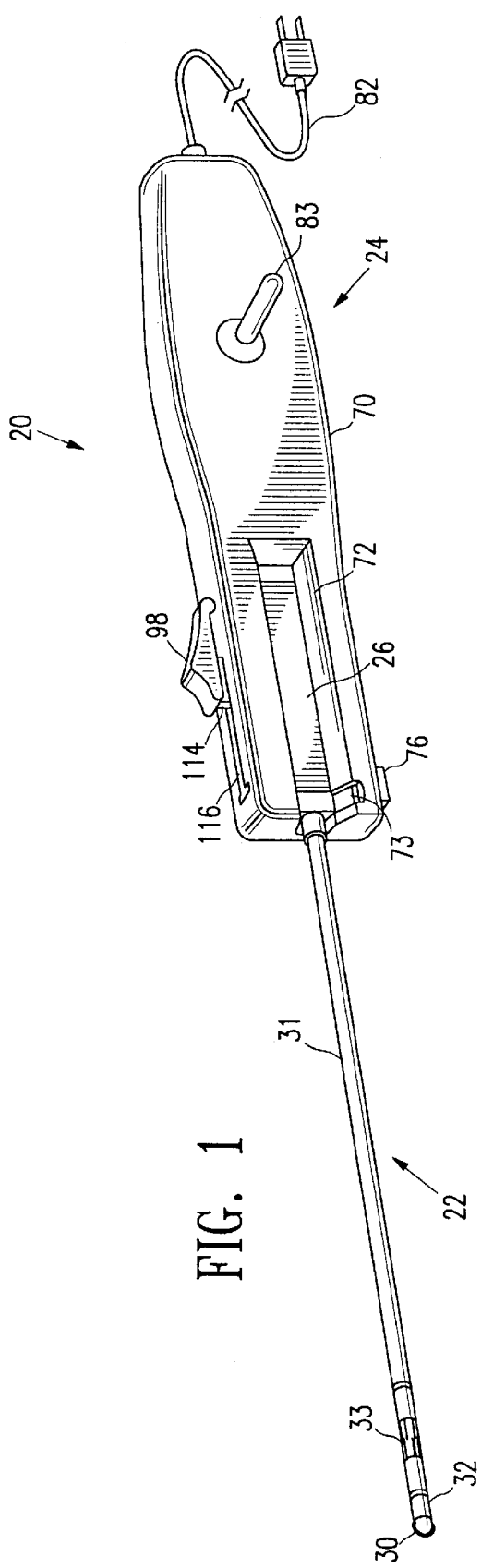
FIG. 1 is a perspective view of an electrosurgical device constructed in accordance with the present invention.
Figure 2:
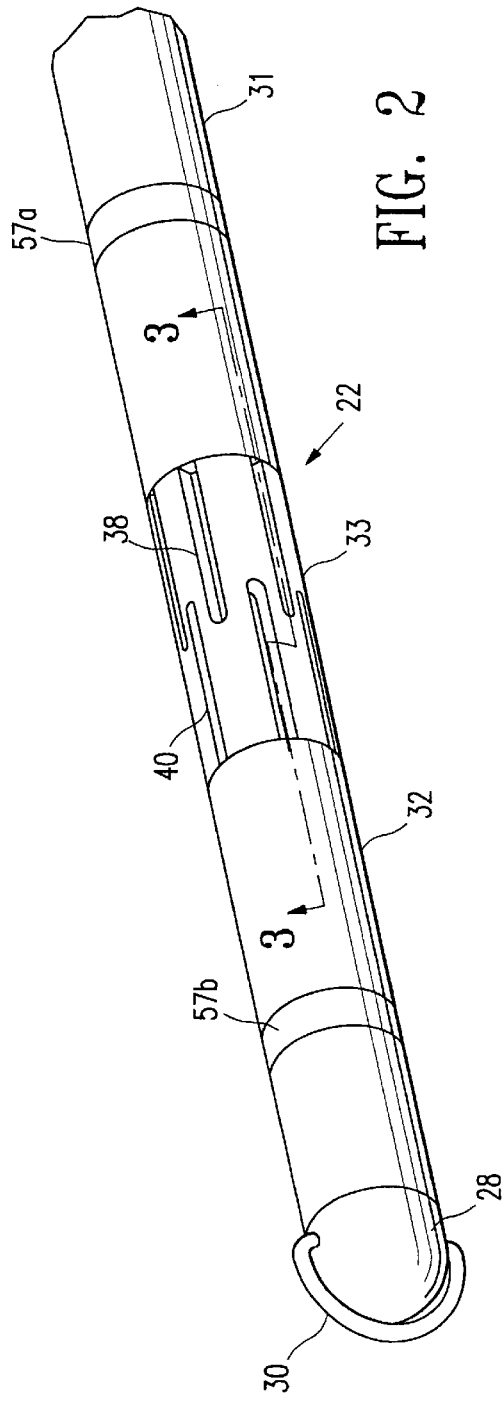
FIG. 2 is a perspective view of the distal end of the tubular trocar of the device illustrated in FIG. 1.

Referring now more particularly to the drawings, FIG. illustrates a particular embodiment of an electrosurgical lesion location device 20 constructed in accordance with the present invention. The lesion location device 20 includes an elongated, tubular trocar portion 22 and a handle portion 24. The proximal end of the trocar portion 22 is fixed to an attachment fitting 26, by which the trocar portion 22 is removably attached to the handle portion 24. A detailed description of the trocar portion 22 will be provided first, followed by descriptions of the attachment fitting 26 and the handle portion 24.

The Trocar Portion

The trocar portion 22 (hereinafter referred to as the trocar 22) extends between the proximal attachment fitting 26 and a hemispherical distal tip 28, the latter preferably being formed of high density polyethylene (HDPE) or the like. The trocar 22 is advantageously provided with a cutting element 30 that extends distally from the distal tip 28 of the trocar 22. The cutting element 30 is preferably an electrosurgical electrode, such as the type disclosed and claimed in commonly-assigned, co-pending U.S. patent application Ser. No. 09/159,467 for "Electrosurgical Biopsy Device and Method," the disclosure of which is incorporated herein by reference. The cutting element or electrode 30 is preferably made of 302 stainless steel wire, of approximately 0.014 in. (approximately 0.36 mm) diameter. As explained below, the electrode 30 is activated with radio frequency (RF) electrical energy to ablate adjacent tissue.

In the preferred embodiment illustrated, the elongate trocar 22 comprises a proximal trocar tube 31 and a distal trocar tube 32, connected by an intermediate member 33. The trocar tubes 31, 32 and the intermediate member 33 may be formed of a sturdy, high impact biocompatible material, such as medical grade polymer (e.g., polycarbonate). In a particular example of the device, the outside diameter of the trocar 22 is approximately 0.125 in. (approximately 3.2 mm), although this dimension is exemplary only.

Electrosurgical techniques have been used in a variety of circumstances. In electrosurgery, high frequency electrical energy is applied through a primary electrode to tissue. The electrical energy flows through the tissue to a return electrode. The tissue adjacent to the primary electrode is ablated, to form an opening in the tissue. The return electrode in monopolar electrosurgery may be an electrode placed on the exterior of the patient's body at a point remote from the primary electrode. In bipolar electrosurgery, the return electrode may be a smaller electrode positioned somewhat near the primary electrode. An exemplary biopsy instrument using electrosurgical techniques is described in International Application Number PCT/US97/15092 (Applicant Ethicon Endo-Surgery), published under the Patent Cooperation Treaty on Mar. 5, 1998 with International Publication Number WO 98/08441. Another electrosurgical biopsy instrument is disclosed and claimed in above-mentioned U.S. patent application Ser. No. 09/159,467.

The illustrated embodiment of the present invention uses monopolar electrosurgical techniques to cut through subcutaneous tissues to reach a target tissue mass. Electrical energy is provided to the electrode 30. The return electrode (not shown) is attached to the patient's body remote from the point at which the trocar 22 is inserted to provide the return electrical path. Alternatively, the electrosurgical aspect of the device may be bipolar, in which the return electrical path is provided by a return electrode (not shown) on the device itself A conductor 34 (FIG. 3) extends axially through the interior of the trocar portion 22 to conduct electrical energy from the handle portion 24 of the device to the electrosurgical electrode 30. The conductor 34 is insulated to maintain electrical isolation from the adjacent components, which may be of conductive metal, as explained below.

Referring now to FIGS. 3 through 6A, the intermediate member 33 of the trocar 22 has a proximal portion 35 that is dimensioned to fit snugly into the open distal end of the proximal trocar tube 31, and a distal portion 36 that is similarly dimensioned to fit snugly into the open proximal end of the distal trocar tube 32. The proximal portion 35 is provided with a first plurality of longitudinal grooves or channels 37 in its outer surface, each of which opens into one of a first plurality of axially-elongate, slot-like apertures 38 that are formed in the intermediate member 33 of the trocar 22. The distal portion 36 of the intermediate member 33 is formed with a second plurality of longitudinal grooves or channels 39, each of which opens into one of a second plurality of axially-elongate, slot-like apertures 40 that are also formed in the intermediate member 33, distally from the first plurality 38. The axial locations of the first and second pluralities of apertures are such that the distal ends of apertures 38 in the first plurality overlap slightly with the proximal ends of the apertures 40 in the second plurality. The apertures 38 in the first plurality alternate with the apertures 40 in the second plurality around the circumference of the trocar portion 22. In the illustrated embodiment, there are six apertures in each of the first and second pluralities, but this number may be varied from as few as two to ten or more. The apertures of each plurality are evenly spaced around the circumference of the trocar.

Figure 3:
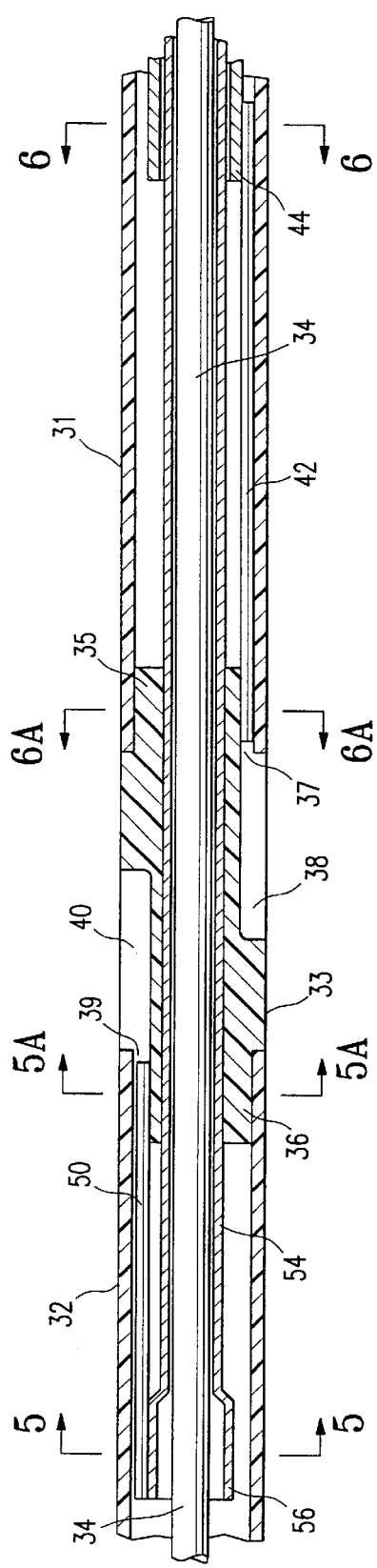
FIG. 3 is a longitudinal cross-sectional view of the tubular trocar, taken along line 3—3 of FIG. 2, showing the locator wires in their retracted position.
Figure 4:
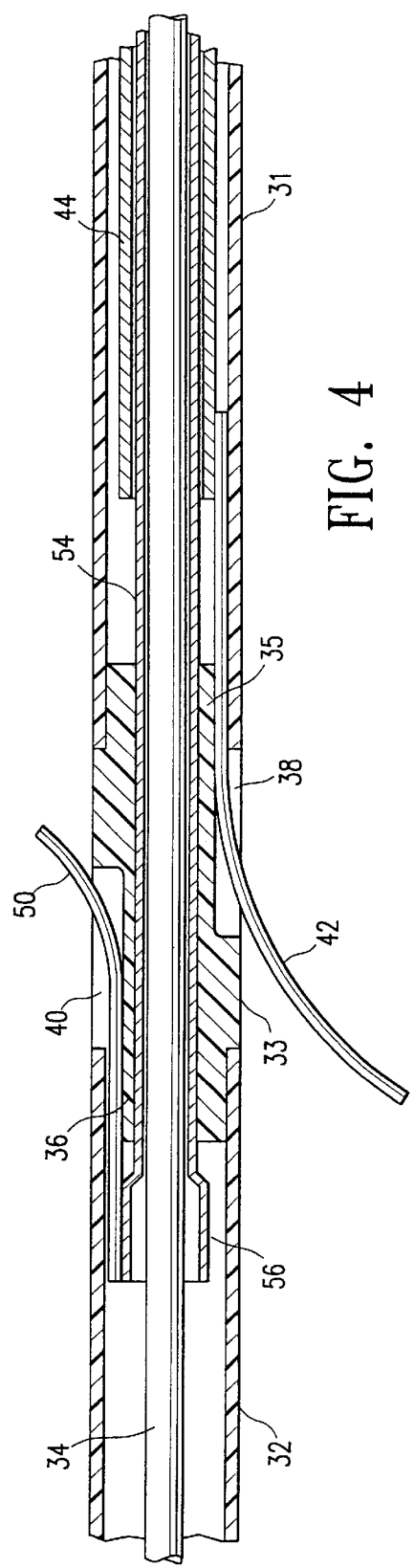
FIG. 4 is a cross-sectional view taken along line 3—3 of FIG. 2, but with the tubular members of the trocar arranged to partially deploy the locator wires.
Figure 5:
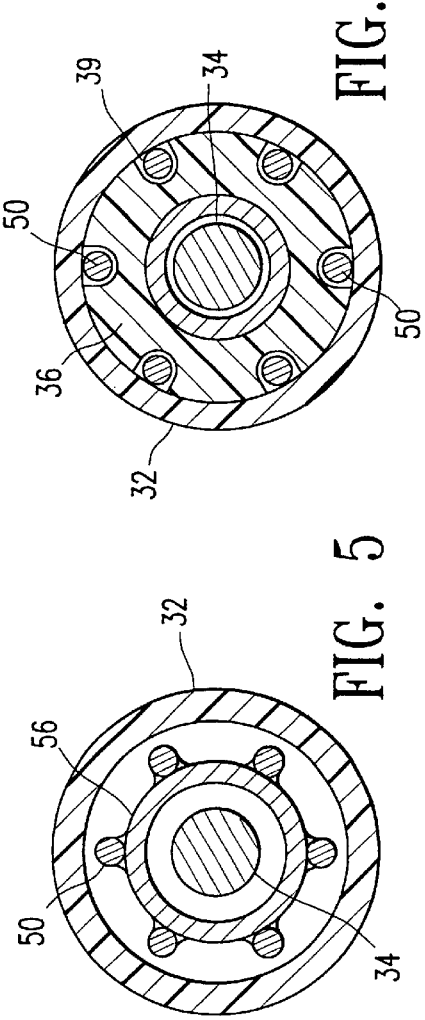
FIG. 5 is a transverse cross-sectional view of the trocar, taken along line 5—5 of FIG. 3.
Figure 5A:
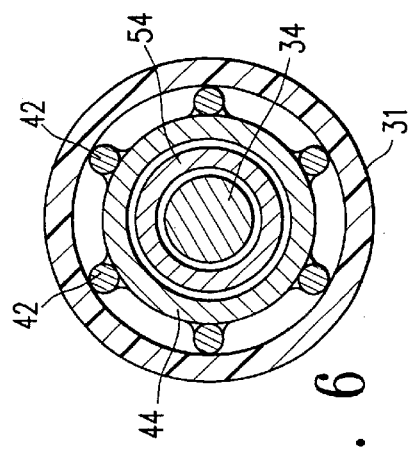
FIG. 5A is a transverse cross-sectional view of the trocar, taken along line 5A—5A of FIG. 3.
Figure 6:
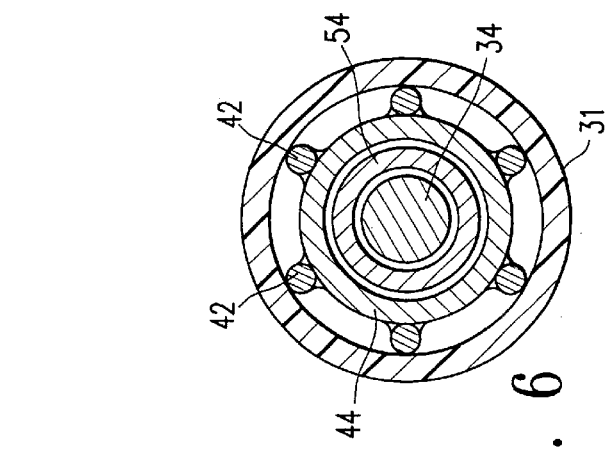
FIG. 6 is a transverse cross-sectional view of the trocar, taken along line 6—6 of FIG. 3.
Figure 6A:
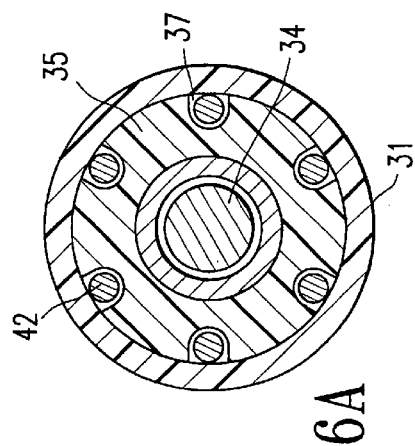
FIG. 6A is a transverse cross-sectional view of the trocar, taken along line 6A—6A of FIG. 3.
Figure 10:
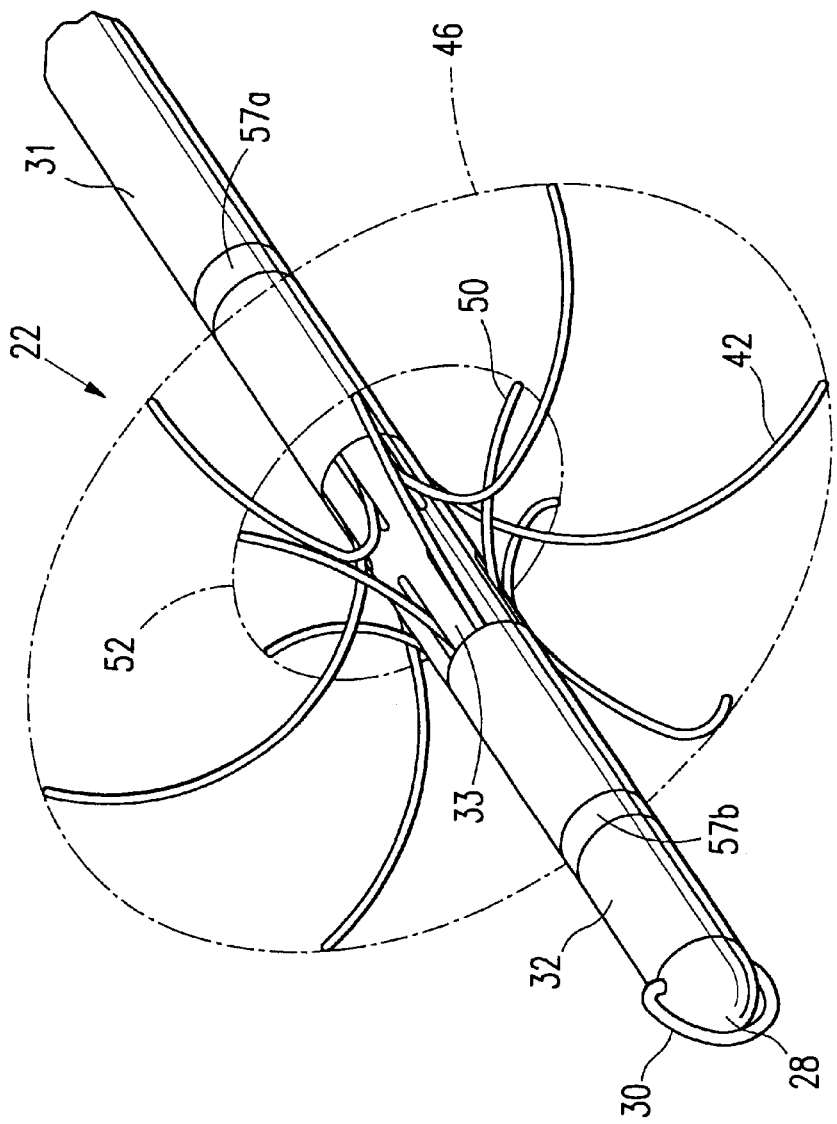
FIG. 10 is a perspective view of the distal portion of the trocar of the device, with the locator wires in their deployed position.
Figure 11:
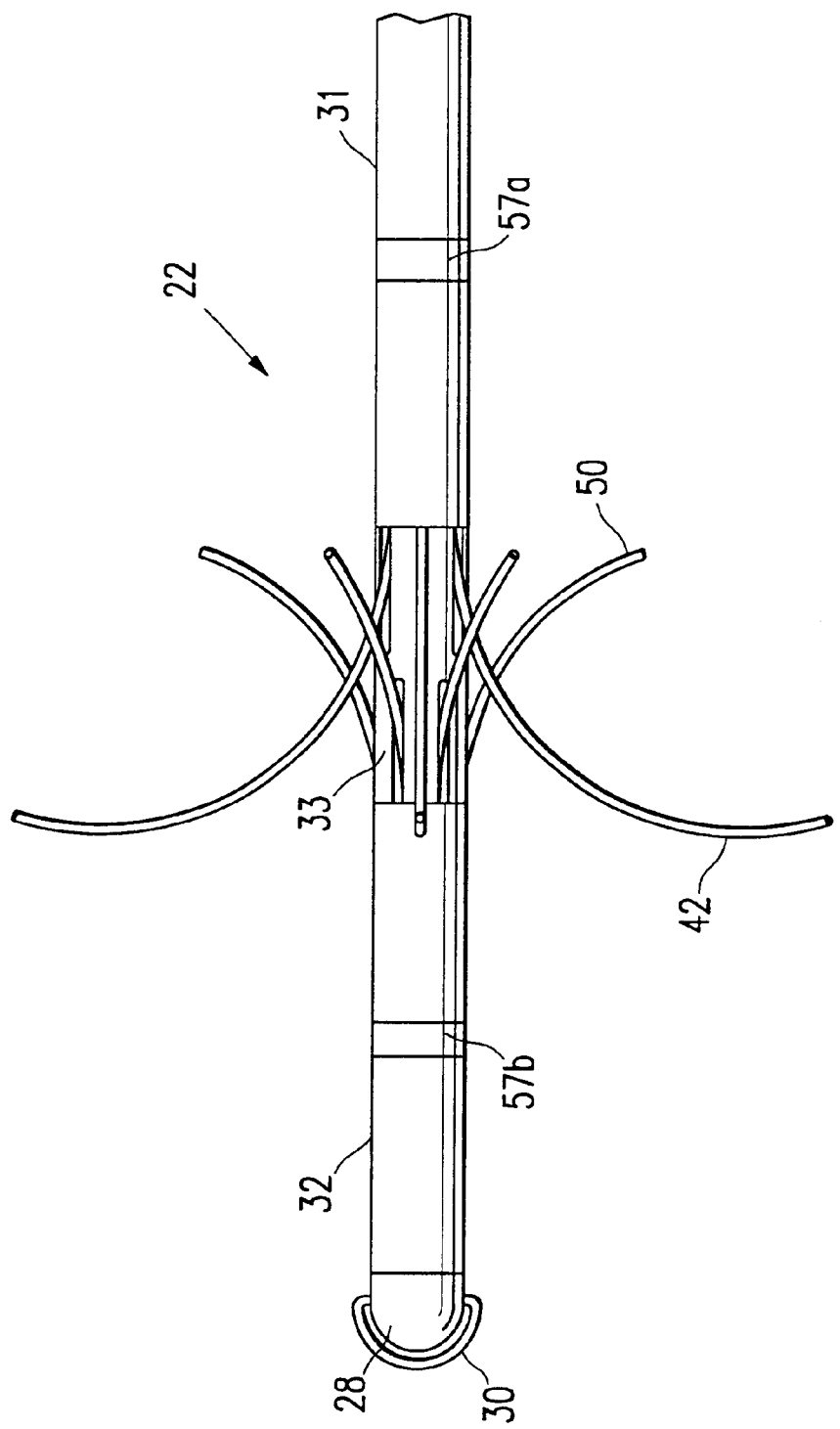
FIG. 11 is a side elevational view of the distal portion of the trocar of the device, with the locator wires in their deployed position.

FIG. 3 shows a first plurality of locator wires 42 contained in a retracted position within the trocar portion 22. Each of the first plurality of locator wires 42 is associated with a corresponding one of the first plurality of apertures 38. Each of the first wires 42 has a proximal end that is attached to the distal end of a first tubular wire-carrying member 44 that is mounted for axial movement within the interior of the proximal trocar tube 31. The distal end of each of the first plurality of wires 42 is movably journaled in one of the channels 37 in the proximal portion 35 of the intermediate member 33. In their retracted position, the first locator wires 42 are aligned substantially longitudinally within the proximal trocar tube 31, and they are fully contained therein. The first locator wires 42 are movable between their retracted position, shown in FIG. 3, and a deployed position, shown in FIGS. 10 and 11. In their deployed position, the first locator wires 42 extend substantially radially from the intermediate member 33 of the trocar 22, to define a first locating perimeter 42 (FIG. 10). The first locator wires 42 may be tensioned to provide a radius of curvature of about 0.295 in. (about 7.5 mm), and, in their deployed position, they form a first locating perimeter 46 with a defined diameter of about 1.2 in. (about 30 mm). This diameter is exemplary only; both small and larger locating perimeters may be defined by using locator wires of different lengths. The first wire-carrying member 44 is longitudinally mounted for axial movement within the interior of the proximal trocar tube 31, between a first or proximal position, and a second or distal position. FIG. 3 shows the first wire-carrying member 44 in its proximal position, corresponding to the retracted position of the first locator wires 42. As shown in FIG. 4, as the first wire-carrying member 44 moves axially toward its distal position, it moves the first locator wires 42 attached to it through the channels 37 of the proximal portion 35 of the intermediate member 33, and then into and through the slot-shaped apertures 38 in the first plurality of apertures. When the distal ends of the first locator wires 42 encounter the slot-shaped apertures 38, the first locator wires 42 are allowed to move radially with respect to the trocar 22. Pre-tensioning the first locator wires 42 so that they tend to bend in an outward, radial direction with respect to the trocar aids in assuring that the first locator wires 42 properly exit the intermediate member 31 of the trocar 22 through the first slotted apertures 38.

Disposed within the distal trocar tube 32 is a second plurality of locator wires 50. The second locator wires 50 have a retracted position in which they extend longitudinally within the distal trocar tube 32 and are fully contained therein. Each of the second plurality of locator wires 50 is associated with a corresponding one of the second plurality of apertures 40. The second locator wires 50 are movable between their retracted position, shown in FIG. 3, and a deployed position, shown in FIGS. 10 and 11. In the deployed position, the second locator wires 50 extend substantially radially from the intermediate member 33 of the trocar 22, to define a second locating perimeter 52. The second wires 50 may also be tensioned to provide a radius of curvature of 0.295 inch (7.5 mm). When the second locator wires 50 are in their deployed position, the distal ends of the second locator wires 50 define a circle having a diameter of approximately 0.47 in. (approximately 12 mm).

The distal ends of the second locator wires 50 are attached to the distal end of a second tubular wire-carrying member 54. The proximal end of each of the second locator wires 50 is movably journaled within one of the channels 39 in the distal portion 36 of the intermediate member 33. The second wire-carrying member 54 is longitudinally mounted for axial movement within the distal trocar tube 32. Specifically, the second wire-carrying member 54 is carried co-axially within the hollow interior of the first wire-carrying member 44, extending distally into the interior of the distal trocar tube 32, after slidably passing through an axial bore in the intermediate member 33.

The second wire-carrying member 54 is axially movable between a distal position (FIG. 3), corresponding to the retracted position of the second locator wires 50, and a proximal position, corresponding to the deployed position of the second locator wires 50. As shown in FIG. 4, as the second wire-carrying member 54 moves axially from its distal position to its proximal position, the second wire-carrying member 54 moves the second locator wires 50 through the journaling channels 39 in the intermediate member 33 and into the second slot-shaped apertures 40. When the distal ends of the second locator wires 50 encounter the slot-shaped apertures 40, the second locator wires 50 begin to move radially with respect to the trocar. Pretensioning the second locator wires 50 so that they tend to bend in an outward, radial direction with respect to the trocar aids in assuring that the second locator wires 50 properly exit the trocar through the second slot-shaped apertures 40.

The proximal portion 35 of the intermediate member 33 provides a stop to limit the axial movement of the first wire-carrying member 44 in the distal direction, away from the handle portion 24 of the device (see FIG. 1). When the distal end of the first wire-carrying member 44 engages the proximal portion 35 of the intermediate member, the first wire-carrying member 44 is at its distal position, and the first locator wires 42 are fully deployed.

In the preferred form, the distal end of the second wire-carrying member 54 is diametrically enlarged to provide a flared end 56, to which the second locator wires 50 are attached. The diameter of the flared end 56 is greater than the diameter of the axial bore through the intermediate member 33, so that the distal portion 36 of the intermediate member 33 provides a stop to limit the axial movement of the second wire-carrying member 54 in the proximal direction. When this limit is reached, the second wire-carrying member 54 is at its proximal position, which corresponds to the second locator wires 50 being fully deployed.

Each of the first locating wires 42 and the second locating wires 50 corresponds to one of the first apertures 38 and second apertures 40, respectively. In the illustrated embodiment, six first locating wires 42 and six second locating wires 50 are uniformly spaced around the trocar. In other embodiments, the number of first locator wires 42 may differ from the number of second wires 50, and the number of each may vary from as few as two to ten or more. Furthermore, the locator wires in each plurality (and especially the first plurality 42) may be of different lengths to provide locating perimeters of different shapes and configurations. For example, the locator wires 42 of the first plurality may be dimensioned to provide a hemispherical perimeter to access target tissue masses that are near the patient's chest wall, or they may provide an asymmetrical perimeter if the target tissue mass is near the surface of the patient's skin. Any configuration can be provided when it is desired to avoid piercing an adjacent organ, or penetrating an adjacent cavity.

When the locating wires 42, 50 that are respectively in the first and second locator wire pluralities are deployed, their tips define the first and second locating perimeters 46, 52, respectively. The curvature of the first locating wires 42 in the proximal direction and the curvature of the second locator wires 50 in the distal direction preferably results in the first and second perimeters 46, 52 being substantially coplanar (defining a plane that is transverse to the axis of the trocar 22). Alternatively, the first perimeter 46 may define a plane that lies a short distance proximally from the plane defined by the second perimeter 52.

When the trocar 22 is inserted through a target tissue mass, as guided by mammography, ultrasound, or other techniques, the first and second locator wires 42, 50 are deployed. When deployed, the first and second locator wires respectively extend into the tissue surrounding a target tissue mass (such as a suspected lesion or tumor) in axially opposite directions, thereby securely anchoring the trocar in the tissue. Accordingly, the trocar is less prone to move within the tissue or to be inadvertently removed therefrom, and thus it provides a more accurate guide for subsequent surgery than has previously been possible. Thus, this anchoring action reduces the possibility that the trocar will shift position or become dislodged before the surgeon has the opportunity to perform the appropriate surgery. Furthermore, the first locating perimeter 46 may be used to define the periphery of the target tissue mass. Thus, while both pluralities of locator wires are secured within the target tissue mass and thus locate and identify it, the first locator wires 42 also help identify the outer periphery of the target mass, with perhaps an added margin of tissue that is identified for removal with the target tissue mass.

In their deployed positions, the distal tips of the first locator wires 42 extend farther from the trocar than the distal tips of the second locator wires 50. To provide this capability, the first wire-carrying member 44 has a range of axial movement that is greater than the range of axial movement of the second wire-carrying member 54. Preferably, the range of axial movement of the first wire-carrying member 44 is about twice the range of axial movement of the second wire-carrying member 54. The mechanism that provides these respective ranges of movement is described below in the description of the handle portion of the invention.

Furthermore, the first and second locator wires 42, 50 are electrically energized to provide monopolar electrosurgical tissue penetration with minimal deployment force. Optionally, the continued electrical energization of the locator wires after deployment may result in tissue desiccation that facilitates the visualization of the target tissue mass by means of color and/or texture differentiation from surrounding tissue. In this embodiment, the first and/or second locating wires may be electrically connected to a source (not shown) of electrical energy to provide for electrosurgical penetration. For this purpose, the first and second locating wires 42, 50 may be about 0.009 in. (0.23 mm) in diameter, and are advantageously formed of 17-7 stainless steel or an equivalent. The wires may be coated (except for their distal ends) with a polymer having a high dielectric strength, so that the tip of each locating wire 42, 50 is the only part of the wire that is energized at the time the wires are deployed from the trocar. In such an embodiment, the first and second wire-carrying elements 44, 54 are made of electrically conductive metal tubing to provide an electrical path along the trocar from the handle portion 24 (FIG. 1) to the locator wires 42, 50. For example, the first and second wire-carrying members 44, 54 may be formed of stainless steel.

Proximal and distal guide marks 57a, 57b may advantageously be provided on the outer surface of the trocar 22. The proximal mark 57a is spaced a small distance proximally from the first apertures 38, while the distal mark 57b is spaced a small distance distally from the second apertures 40. The distance between the marks 57a, 57b is preferably approximately equal to the diameter of the first locator wire perimeter 46, thereby defining in the axial direction a perimeter that is substantially equal to the first perimeter 46 defined by the first locator wires 42. The marks 57a, 57b may be made with a material that is easily visible to the surgeon or that is readily detected in the mammography, x-ray, ultrasound, or other radiological examination. Alternatively, they can be illuminated via fiber optic means (not shown).

Figure 15:
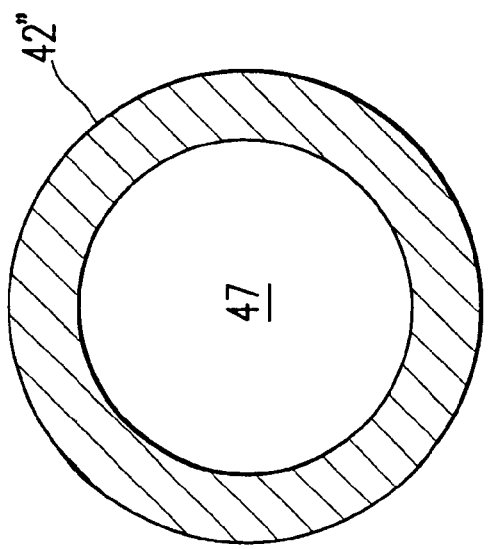
FIG. 15 is a cross-sectional of another modified form of a locator wire that may be used in the present invention.
Figure 14:
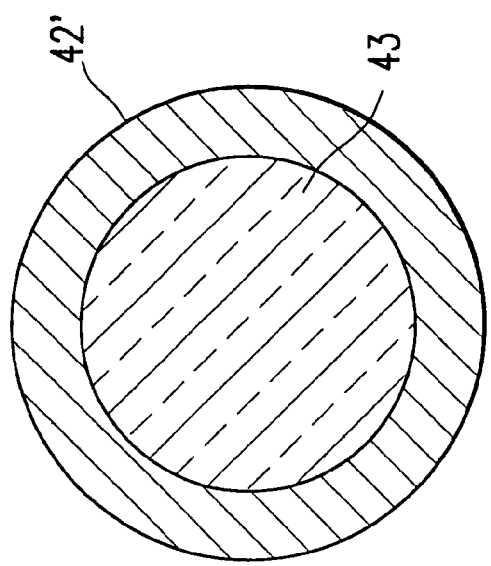
FIG. 14 is a cross-sectional of a modified form of a locator wire that may be used in the present invention.

It may be advantageous to modify the one or more of the first or second locating wires 42, 50 for better visualization. For example, as shown in FIG. 14, a locator wire 42' may be formed with a hollow interior and contain an optical fiber 43 that extends out of an open end of the wire. This allows the tip of the locating wire to be illuminated for easier visualization of the target tissue mass and the surrounding tissue as a guide during surgery. Alternatively, or in addition, one or more of the first or second locator wires 42, 50 may be formed as an open-ended hollow wire 42", as shown in FIG. 15, to provide a passage 47 for the injection of a dye into the local region of tissue, to assist in guiding the surgeon in the subsequent surgery.

The Attachment Fitting

Figure 13:
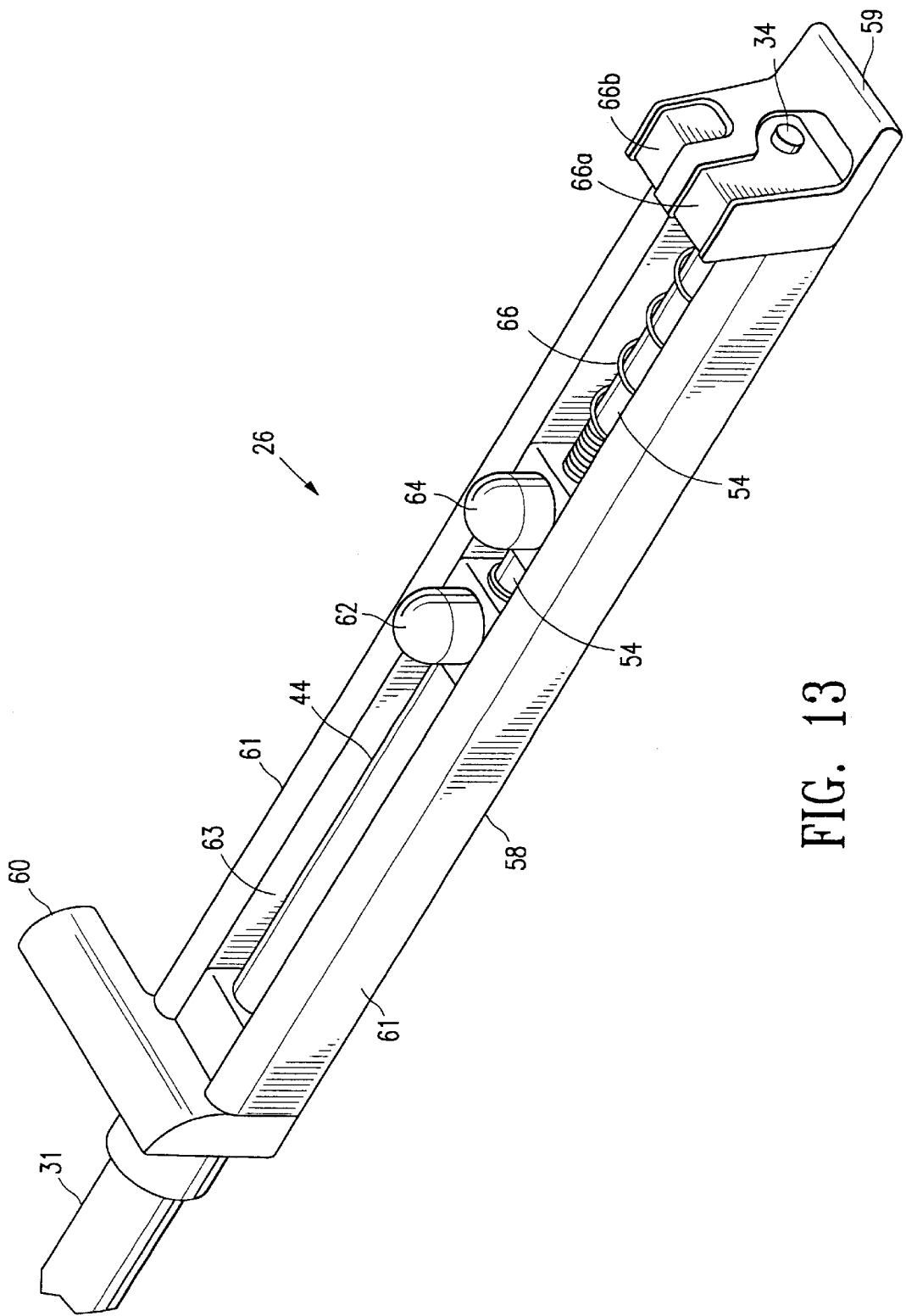
FIG. 13 is a perspective view of the attachment fitting by which the trocar of the device is removably attached to the handle portion.

The attachment fitting 26 is best shown in FIG. 13. It comprises a narrow, elongate housing 58 having a distal end fixed to the proximal end of the proximal trocar tube 31, and a proximal end formed into a lip 59. A transverse finger 60, the purpose of which will be described below, extends laterally from the housing 58 near its distal end. The housing 58 includes a pair of opposed side walls 61 that define a channel 63. The first and second wire-carrying members 44, 54, extend into the channel 63 through an opening (not shown) at the distal end of the housing 58. The first wire-carrying member 44 has a proximal end to which is fixed a first attachment lug 62. The second wire-carrying member 54 has a proximal end, extending outwardly from the open proximal end of the first wire-carrying member 44, to which is fixed a second attachment lug 64. The attachment lugs 62, 64 extend out of the channel opening defined by the ends of the side walls 61.

The proximal end of the housing 58 is provided with first and second electrical contacts 66a, 66b. The first contact 66a is electrically connected to the central conductor 34 that extends proximally out of the proximal end of the second wire-carrying member 54. The second contact 66b is electrically connected by a coiled wire to the second wire-carrying member 54. The first and second wire-carrying members 44, 54 are formed of an electrically conductive metal, and the second wire carrying member 54 is contained coaxially within the first wire carrying member 44, establishing physical contact between the two wire-carrying members 44, 54. Thus, an electrical path is established from the second wire carrying member 54 to the first wire-carrying member 44.

The Handle Portion

The handle portion 24 is described with reference to FIGS. 1, 7, 8, 9, 12, 16, and 17. As best shown in FIG. 1, the handle portion 24 has an outer housing 70 that is dimensioned and configured to be held comfortably by the radiologist or surgeon operating the device, while being large enough to enclose the internal electrical and mechanical components that will be described below. The housing 70 is advantageously formed of a rigid, nonconductive polymer material.

The housing 70 includes a longitudinal slot 72 configured and dimensioned for receiving the attachment fitting 26. The transverse finger 60 of the attachment fitting 26 fits into a short transverse slot 73 (FIG. 12) that branches off the longitudinal slot 72 near its distal end. A latch 74 (best shown in FIGS. 8 and 9) extends across the transverse slot 73 to engage the finger 60. When the finger 60 is in the transverse slot 73 and the latch 74 engages the finger 60, the latch 74 holds the attachment fitting 26 in the longitudinal slot 72. The slot 72 has an opening 75 (FIG. 12) at its proximal end that receives the lip 59 at the proximal end of the attachment fitting 26, thereby releasably securing the proximal end of the fitting 26 in the slot 72. A spring 77 (FIGS. 8 and 9) biases the latch 74 in place across the transverse slot 73. A thumb release 76 attached to the latch 74 permits the user to overcome the bias force of the spring 75 to release the latch 74, freeing the finger 60, and thereby permitting the removal of the trocar 22 and the attachment fitting 26 from the handle 24. The thumb release 76 is arranged to permit one-handed release of the trocar portion 22 from the handle portion 24 by a person holding the handle portion 24.

First and second electrical contacts 80, 81 in the longitudinal slot 72 (FIG. 12) provide electrical connections between the handle portion 24 and the first and second contacts 66a, 66b, respectively, in the attachment fitting 26. As described above, the first and second wire-carrying members 44, 54 may be electrically conductive to provide such electrical connectivity to the locator wires 42, 50. The attachment fitting 26 is configured so that when it is inserted into the elongate slot 72 of the handle portion 24, appropriate electrical contact is made between the handle portion contacts 80, 81 and the attachment fitting contacts 66a, 66b, respectively. For example, the trocar conductor 34 leading to the electrosurgical electrode 30 may make electrical contact with the first handle contact 80 through the first attachment fitting contact 66a, and the first and second wire-carrying members 44, 54 may make electrical contact with the second handle contact 81 through the second attachment fitting contact 66b.

Electrical energy is provided to the handle electrical contacts 80, 81 from a power cord 82 (FIG. 1). Power may be supplied to the power cord 82 by any suitable, commercially-available electrosurgical generator (not shown), preferably one that generates an output signal having a frequency of about 0.5 MHz to about 1 MHz. Such generators typically have a foot-pedal operated power switch (not shown) for turning the electrical power to the handle on and off.

A control lever 83 on the handle portion 24 allows the surgeon selectively to energize the electrosurgical electrode 30 and the locator wires 42, 50. The control lever 83 is preferably placed on one side of the handle portion 24 so that the surgeon can manipulate the control lever 83 with a thumb or finger of the same hand the surgeon is using to hold the handle portion 24.

The control lever 83 preferably has two positions: a first position in which electrical energy is provided to the first handle contact 80 for providing electrical energy to the electrosurgical electrode 30; and a second position in which electrical energy is provided to the second handle contact 81 for energizing the locator wires 42, 50. Specifically referring to FIGS. 16 and 17, the control lever 83 is mounted on a shaft 84 that extends into the housing 70. Mounted on the shaft 84 within the housing is a switch actuator 85 that rotates with the shaft 84. The switch actuator 85 is connected to one end of an elongate, flexible conductive switching element 86, the other end of which is connected to a terminal 87, which, in turn, is electrically connected to wires from the power cord 82. First and second switch contacts 88a, 88b are provided in the housing, the first contact 88a being connected by a first wire conductor 89a to the first housing contact 80, and the second contact 88b being connected by a second wire conductor 89b to the second housing contact 81. The switch actuator has a first position (FIG. 16), corresponding to the first position of the control lever 83, in which the switch element 86 is brought into contact with the first switch contact 88a, and a second position (FIG. 17), corresponding to the second position of the control lever 83, in which the switch element 86 is brought into contact with the second switch contact 88b.

Means (not shown) may optionally be included to provide different power levels to the handle contacts 80, 81. For example, when the switch actuator 85 is in the first position, power between 60 and 104 watts at 1 MHz may be supplied to the first handle electrical contact 80. When the switch actuator 85 is in the second position, power between 43 and 55 watts at 1 MHz may be supplied to the second handle electrical contact 81. The electronic circuitry to provide these dual power levels is considered to be well within the level of ordinary skill in the pertinent arts.

The handle portion 24 includes a deployment mechanism 90 (see FIGS. 8 and 9) to control movement of the first and second tubular elements 44, 54 of the trocar for deploying the first and second locator wires 42, 50 (see FIGS. 3 and 4). The deployment mechanism 90 includes a first, proximal slider 92, and a second, distal slider 94. As will be apparent from the following description, the first, proximal slider 92 controls the movement of the first tubular element 44 for deploying the first locator wires 42. The second, distal slider 94 controls the movement of the second tubular element 54 for deploying the second locator wires 50.

In the embodiment illustrated, the deployment mechanism 90 moves the first and second sliders 92, 94 simultaneously in opposite directions. The simultaneous movement of the first and second sliders 92, 94 simultaneously moves the first and second wire-carrying members 44, 54, thereby also simultaneously deploying the first and second locator wires 42, 50. A connecting element 96 links the first slider 92 and the second slider 94. The connecting element 96 includes an elongate body that has a first end slot 102 and a second end slot 104. The first end slot 102 engages a pin 103 on the first, proximal slider 92. The second end slot 104 engages a pin 105 on the second, distal slider 94. The connecting element 96 is pivotally secured to the body of the handle portion 24 at a pivot point 108.

As noted above, the range of axial movement within the trocar of the first wire-carrying member 44 that deploys the first locator wires 42 is approximately twice the range of axial movement of the second wire-carrying member 54 that deploys the second locator wires 50. The deployment mechanism 90, and particularly the connection 96 between the first slider 92 and the second slider 94, provides a greater range of movement for the first slider 92 than the second slider 94. The pivot point 108 is positioned along the body of the connecting element 96 so that the first end of the connecting element 96 (with the first slot 102) has a longer range of movement than the second end of the connecting element 96 (with the second slot 104). The configuration causes the second slider to move about one half the distance the first slider moves. The first end slot 102 is approximately twice the length of the second to end slot 104 to accommodate this different range of movement.

Figure 7:
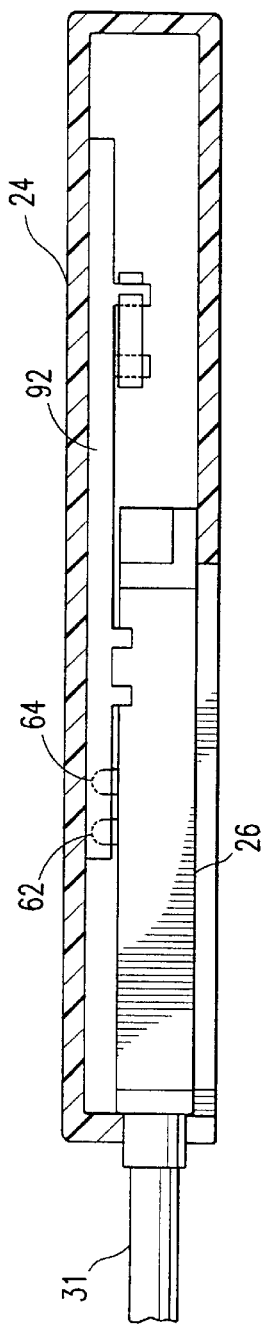
FIG. 7 is a top view, partially in cross-section, of the handle portion of the device illustrated in FIG. 1.
Figure 12:
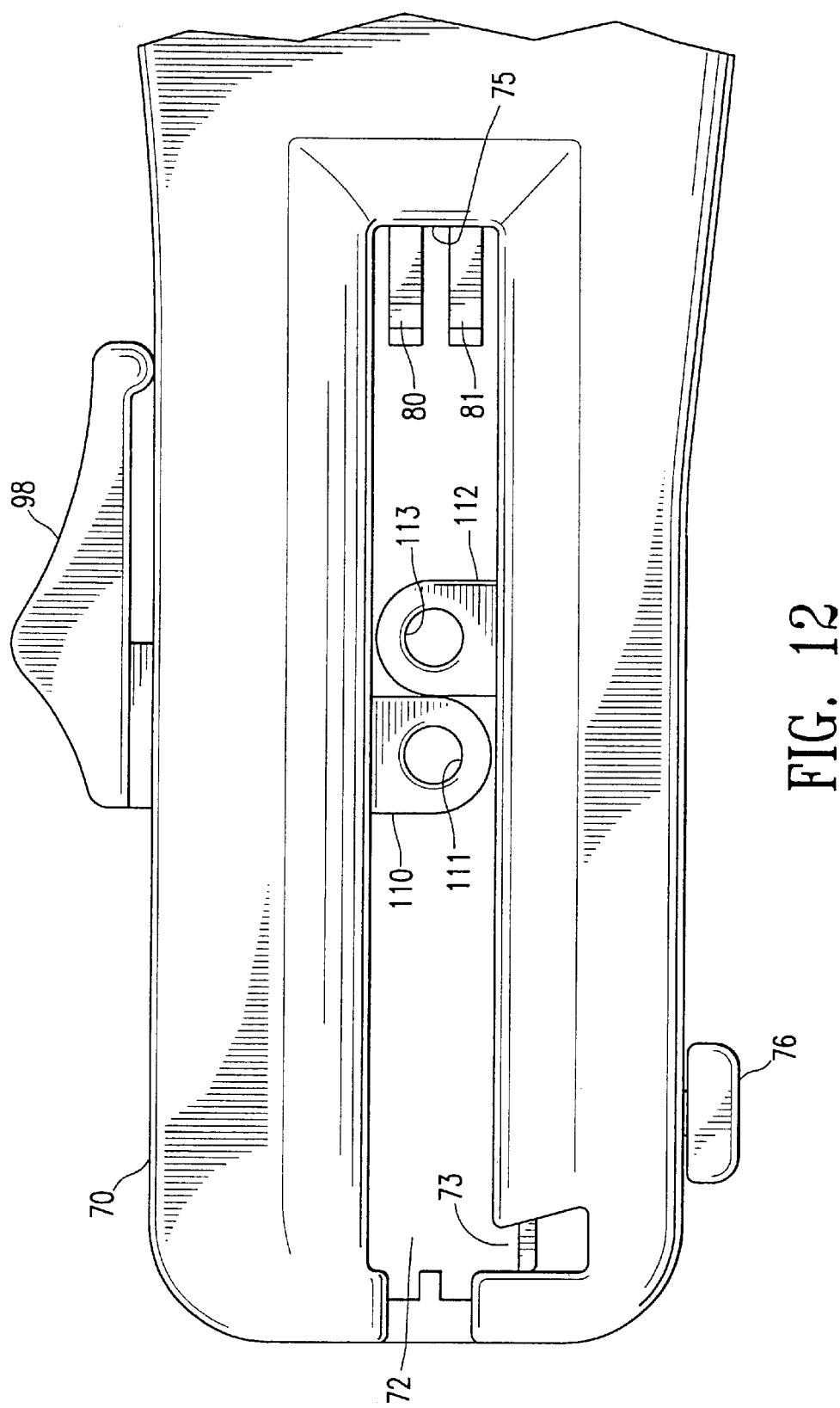
FIG. 12 is a side elevational view of a part of the handle portion of the device, with the trocar removed.

The connection between each slider 92, 94 and its respective corresponding wire-carrying member 44, 54 is provided by a transverse extension 110, 112 at the distal end of each slider 92, 94, respectively. As best shown in FIG. 12, the extension 110 of the first slider 92 has an aperture 111, and the extension 112 of the second slider 94 has an aperture 113. As shown in FIG. 7, the aperture 111 on the first slider 92 receives the attachment lug 62 on the first wire-carrying member 44, and the aperture 113 on the second slider 94 receives the attachment lug 64 of the second wire-carrying member 54.

Figure 8:
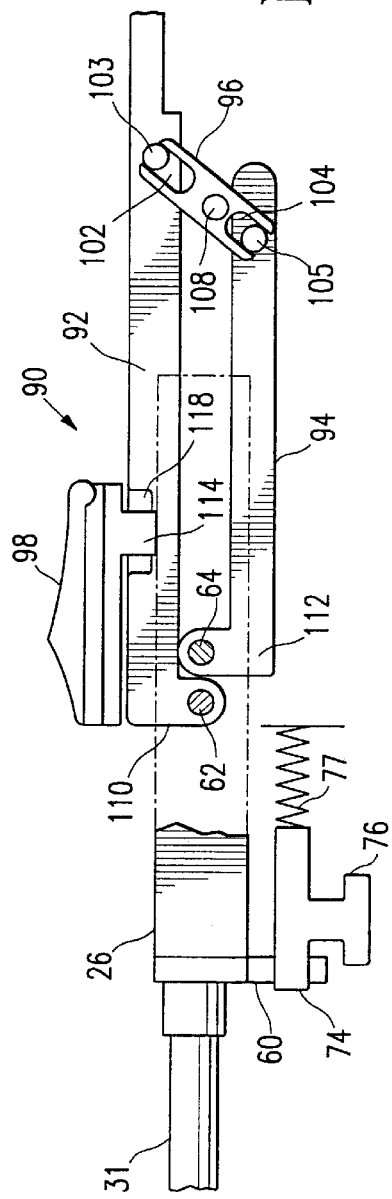
FIG. 8 is a view of the interior of the handle portion of the device illustrated in FIG. 1, with the outer shell of the handle portion removed, showing the mechanism arranged for the locator wires of the device to be in their retracted position.
Figure 9:
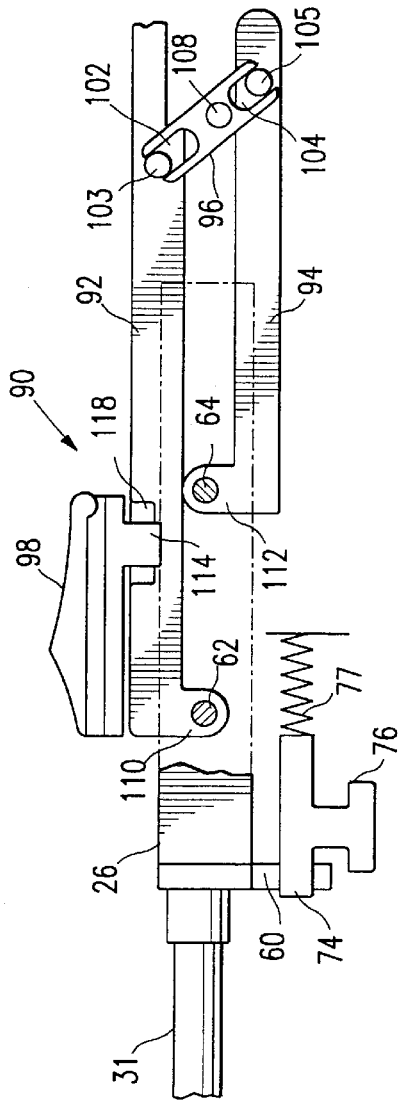
FIG. 9 is a view similar to that of FIG. 8, showing the mechanism arranged for the locator wires of the device to be in their deployed position.

A thumb control 98 positioned on the top side of the handle portion 24 is directly attached to the first, proximal slider 92. Specifically, the thumb control 98 includes a pin 114 that rides in a slot 116 in the top of the handle housing 70 (FIG. 1). The pin 114 extends into the interior of the housing 70 and is received in a recess 118 in the first slider 92, as shown in FIGS. 8 and 9. As the thumb control 98 is moved longitudinally in the slot 116 from a proximal position (shown in FIG. 8) to a distal position (shown in FIG. 9) the thumb control 98 moves the first slider 92 longitudinally from its proximal position toward its distal position. When the attachment fitting 26 is installed in the handle portion 24, the first slider 92 is directly connected to the first tubular member 44, so the movement of the first slider 92 toward its distal position moves the first tubular member 44 toward its distal position, deploying the first locator wires 42. As the first slider 92 is moving from its proximal position to its distal position, the connecting element 96 connecting the first and second sliders 92, 94 causes the second slider 94 to simultaneously move from its distal position toward its proximal position, though at a rate less than (on the order of one-half) the rate of movement of the first slider 92. The second slider 94 is connected to the second tubular member 54, so that the movement of the second slider 94 directly corresponds to the movement of the second tubular member 54. Therefore, the movement of the second slider 94 from its distal position to its proximal position moves the second tubular member 54 from its distal position (in which the second locator wires 50 are retracted) toward its proximal position (in which the second locator wires are deployed).

Figure 16:
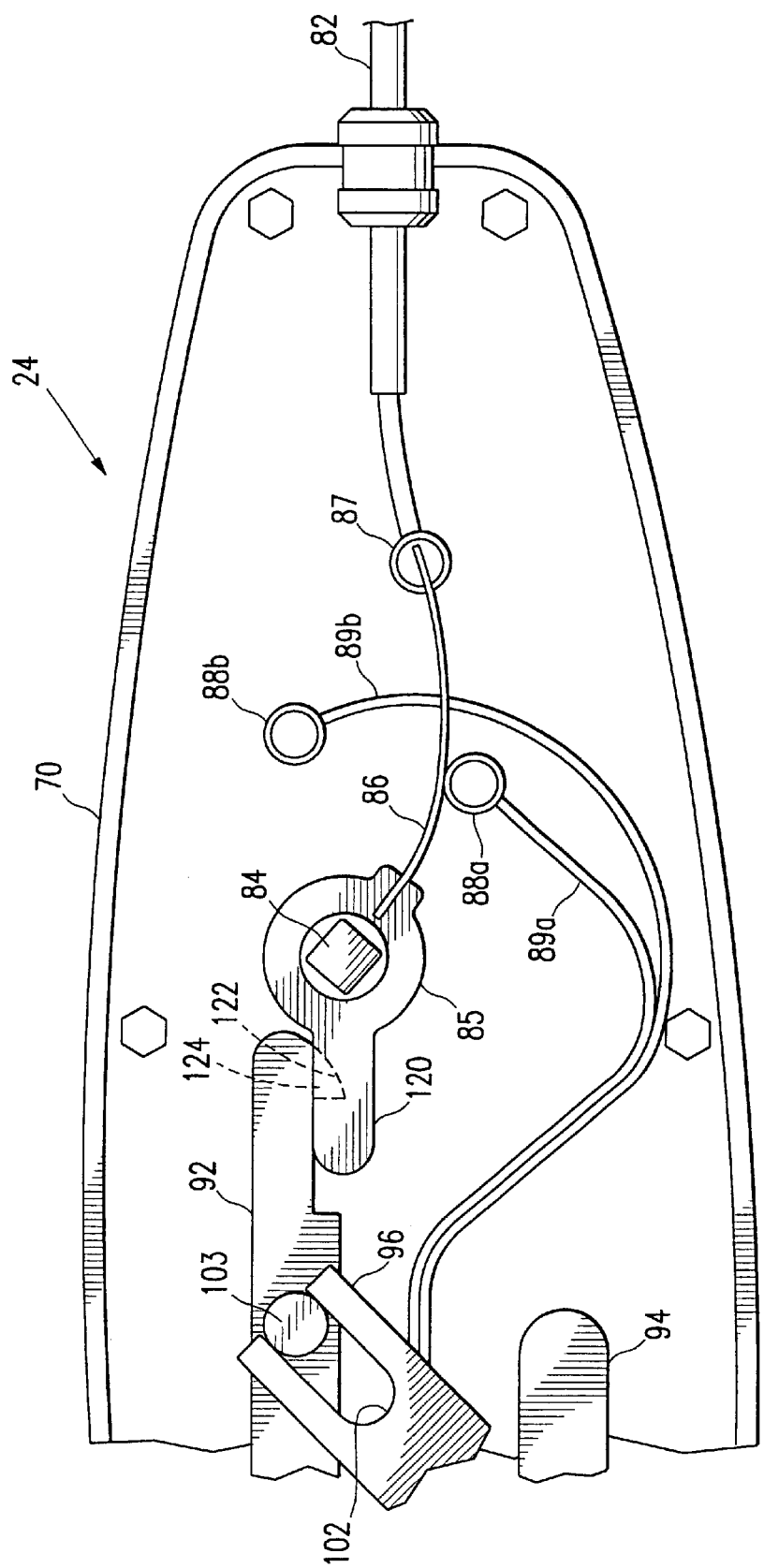
FIGS. 16 and 17 are cross-sectional views of a part of the handle portion of the present invention, showing the electrical switching mechanism and the locking mechanism used in the preferred embodiment.
Figure 17:
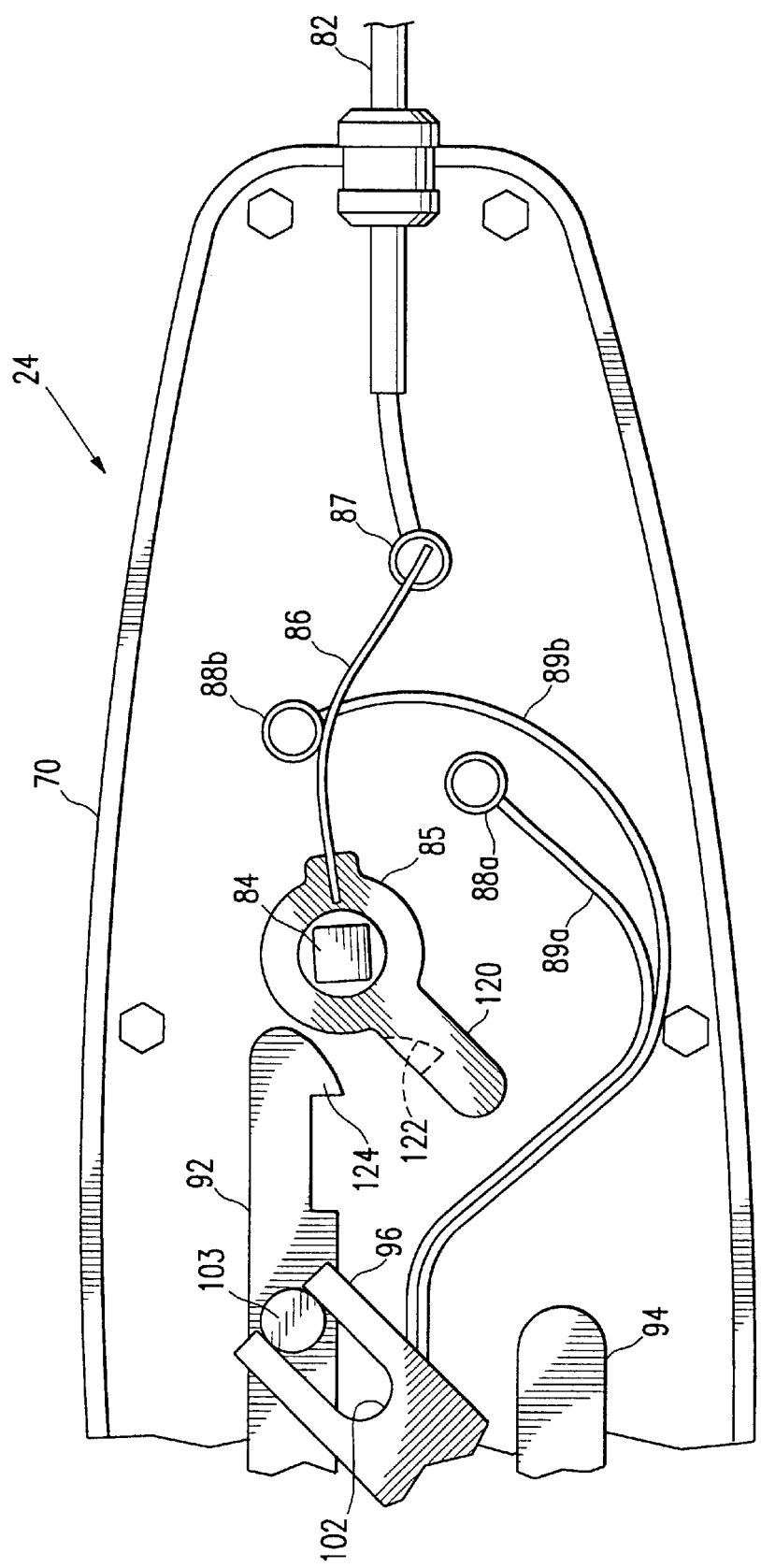

It may be advantageous to provide a lock-out mechanism between the control lever 83 and the locator wire deployment mechanism 90, whereby deployment of the locator wires 42, 50 is prevented when the lever 83 is positioned for energizing the electrode 30. An exemplary lock-out mechanism is shown in FIGS. 16 and 17. As shown, the switch actuator 85 is formed with a lobe or finger 120 having a notch 122. When the switch actuator 85 in the first position (in which the cutting element 30 is energized, as described above), the notch 122 engages a detent 124 at the proximal end of the first slider 92. This engagement locks the first slider 92 in its proximal position, thereby blocking the movement of both sliders 92, 94 due to their linkage by the linking element 96. With both sliders 92, 94 inhibited from movement, deployment of the locator wires 42, 50 is prevented. When deployment of the locator wires 42, 50 is desired, the switch actuator 85 is rotated by the control lever 83 to its second position (FIG. 17), releasing the detent 124 from the notch 122, and thereby unlocking the sliders 92, 94.

Operation

In operation, a target tissue mass is identified through conventional visualization means, as described above. A small, shallow incision is then made (e.g., by a scalpel) at an appropriate place on the patient's body to provide an entry site for the trocar 22. To operate the electrosurgical lesion location device 20 to localize and mark target tissue mass, a surgeon places the control lever 83 its first position to supply electrical energy to the electrosurgical electrode 30. The distal tip 28 of the trocar 22 is inserted into the incision and into the subcutaneous tissue. The energized cutting electrode 30 cuts into the tissue until the distal trocar tip 28 extends through the target tissue mass and the intermediate portion 33 is located within the target tissue mass, as indicated by mammography or other visualization means.

Once the trocar 22 is in place in the tissue, the surgeon moves the control lever 83 to its second position to activate the electrosurgical tips of the first and second locator wires 42, 50. The surgeon slides the thumb control 98 from its proximal position to its distal position. As described above, this movement of the thumb control 98 deploys the first and second locator wires 42, 50 into the tissue, to anchor the trocar 22 in place, and identify the tissue to be removed in subsequent surgery. Preferably, the trocar 22 is positioned so that the locator wires 42, 50 extend to the periphery of the tissue to be removed, as described above. Once the trocar 22 has been inserted, and anchored with the locator wires 42, 50, the flow of electrical energy to the trocar 22 is turned off by use of the foot pedal switch of the generator (as described above). The thumb release 76 is manipulated to release the finger 60 of the attachment fitting housing 58, allowing the trocar 22 to be removed from the handle 24.

The patient can then be removed to the surgical operating room, with the trocar portion 22 remaining in place, for the surgeon to perform the appropriate surgery. The trocar portion 22 is unlikely to shift position in the tissue as the patient is removed because the locator wires 42, 50 assist in holding the trocar in position. This is true even when the tissue is removed from a compressed condition on a mammography apparatus. When the surgeon opens the tissue region, the trocar and the deployed locator wires 42, 50 provide the surgeon direct indication of the area of tissue to be removed or otherwise operated upon.

Those skilled in the art will recognize that various modifications may be made to the specific embodiment illustrated above without departing from the spirit of the present invention. For example, numerous modifications may be made to the handle portion of the device, the mechanism for attaching the proximal end of the trocar to the handle portion of the device, and to the specific mechanism for deploying the locator wires. In addition, while the preferred embodiment employs an electrosurgical electrode 30 as the incision-making element, a non-electrical cutting element may work satisfactorily in some applications. Furthermore, although the preferred embodiment described above employs two pluralities of locator wires working in opposition (that is, they are deployed in radially-opposite directions), a device employing only a single plurality of locator wires may be suitable in certain procedures. Moreover, although the preferred embodiment described above employs first and second pluralities of locator wires that are deployed simultaneously (in unison), it may be acceptable to deploy the first and second pluralities of locator wires sequentially. These and other modifications that may suggest themselves are considered to be within the spirit and scope of the invention, as defined in the claims that follow.

What is claimed is:

1. A device for localizing a target tissue mass in the body of a patient, comprising:

an elongate, hollow, tubular trocar portion having a proximal end portion and a distal end; and a first plurality of locator wires disposed in the trocar portion and movable between a retracted position in which they are fully contained within the trocar portion, and a deployed position in which they extend radially from the trocar portion distal to their retracted position; and a second plurality of locator wires disposed in the trocar portion and movable between a retracted position in which they are fully contained within the trocar portion, and a deployed position in which they extend radially from the trocar portion proximal to their retracted position.

2. The device of claim 1, further comprising an electrosurgical tissue cutting element at the distal end of the trocar portion.

3. The device of claim 1, wherein the first and second plurality of locator wires respectively define first and second perimeters when they are in their respective deployed positions.

4. The device of claim 3, wherein the trocar portion includes first and second pluralities of circumferentially-spaced apertures through which the first and second pluralities of locator wires respectively extend when they are in their deployed positions.

5. The device of claim 4, wherein the first and second pluralities of locator wires are respectively attached to first and second wire-carrying members disposed axially within the trocar portion for longitudinal movement between respective first positions and second positions, and wherein the first positions of the wire-carrying members correspond to the retracted positions of the locator wires, and the second positions of the wire-carrying members correspond to the deployed positions of the locator wires.

6. The device of claim 5, wherein the first wire-carrying member comprises a first, hollow elongate element disposed axially within the trocar portion and having a distal end to which the first plurality of locator wires are attached, and wherein the second wire-carrying member comprises a second elongate element disposed axially within the first elongate element and having a distal end to which the second plurality of locator wires are attached.

7. The device of claim 9, wherein the first and second wire-carrying members are movable in axially opposite directions to each other when they are respectively moved from their respective first positions to their respective second positions and from their respective second positions to their respective first positions.

8. The device of claim 5, further comprising:

a handle portion;

an attachment fitting fixed to the proximal end portion of the trocar, wherein the first and second wire-carrying members extend into the attachment fitting, and wherein the attachment fitting is removably attachable to the handle portion; and a deployment mechanism in the handle portion and engageable with the first and second wire-carrying members when the attachment fitting is attached to the handle portion to move the first and second wire-carrying members between their respective first and second positions.

9. The device of claim 8, wherein the first position of the first wire carrying member and the second position of the second wire-carrying members are proximal positions and the second position of the first wire carrying member and the first position of the second wire-carrying member are distal positions, and wherein the deployment mechanism comprises:

a first slider engageable with the first wire-carrying member and movable between a proximal position and a distal position;

a second slider engageable with the second wire-carrying member and movable between a proximal position and a distal position;

a linking element connecting the first slider to the second slider so that the second slider moves proximally when the first slider moves distally and the second slider moves distally when the first slider moves proximally; and an actuation element engageable with one of the first and second sliders for moving the one of the sliders between the proximal and distal positions.

10. The device of claim 1, wherein the trocar portion includes a plurality of circumferentially-spaced apertures through which the locator wires extend when they are in their deployed position.

11. The device of claim 10, wherein the locator wires are attached to a wire-carrying member disposed axially within the trocar portion for longitudinal movement between a first position and a second position, and wherein the first position of the wire-carrying member corresponds to the retracted position of the locator wires, and the second position of the wire-carrying member corresponds to the deployed position of the locator wires.

12. The device of claim 1, wherein the locator wires are formed of a conductive metal and wherein the locator wires are configured for connecting to a source of electrical energy for providing an electrosurgical effect when the locator wires are in their deployed position.

13. A method of localizing and marking an identified target tissue mass in the body of a patient, comprising the steps of:

(a) visualizing the target tissue mass;

(b) providing a trocar having a distal end, containing a first plurality of locator wires disposed in the trocar section and movable between a retracted position in which they are fully contained within the trocar portion, and a deployed position distal to their retracted position in which they extend radially from an intermediate portion of the trocar and containing a second plurality of locator wires disposed in the trocar section and movable between a retracted position in which there are fully contained within the trocar portion, and a deployed position proximal to their retracted position in which they extend radially from an intermediate portion of the trocar;

(c) during the visualizing step, and while the locator wires are in their retracted position, inserting the trocar into the body so that the distal end passes through the target mass and so that the intermediate portion of the trocar is within the target tissue mass; and (d) moving the first and second plurality of locator wires from their retracted positions to their deployed positions so that at least some of the locator wires are anchored within the target tissue mass.

14. The method of claim 10, wherein the step of inserting is at least partially performed electrosurgically.

15. The method of claim 13, further comprising the step of electrically energizing at least some of the locator wires as they are moved to their deployed position.

16. The method of claim 15, wherein the step of electrically energizing is continued after the energized locator wires are in their deployed position to dessicate tissue in the proximity of the energized locator wires.

17. The method of claim 13, wherein the first and second pluralities of locator wires are movable in unison from respective retracted positions fully contained within the trocar to first and second respective deployed positions radially extending from the intermediate portion of the trocar, the deployed position of the locator wires in the first and second pluralities respectively defining first and second perimeters, and wherein the moving step comprises the step of moving the locator wires in the first and second pluralities from their respective retracted positions to their respective deployed positions, whereby at least some of the locator wires in the first plurality are anchored in the target tissue mass and at least some of the locator wires in the second plurality are anchored in tissue surrounding the target tissue mass.

18. Apparatus for localizing a target tissue mass in the body of a patient, comprising:
an elongate trocar portion having a proximal end and a distal end;
a cutting element at the distal end of the elongate trocar;
a handle portion; an attachment fitting attached to the proximal end of the trocar portion and configured for removable attachment to the handle portion; and
a first plurality of locator wires that are movable between a retracted position within the trocar portion, and a deployed position distal to their retracted position extending substantially radially from the trocar portion; and
a second plurality of locator wires disposed in the trocar section and movable between a retracted position in which they are fully contained within the trocar portion, and a deployed position proximal to their retracted position in which they extend radially from an intermediate portion of the trocar.

19. The apparatus of claim 18, wherein the cutting element is an electrosurgical cutting element.

20. The apparatus of claim 18, wherein the locator wires of the first plurality of locator wires are connected to a first elongate member longitudinally mounted for axial movement within the trocar portion between a proximal position corresponding to the retracted position of the first plurality of locator wires, and a distal position corresponding to the deployed position of the first plurality of locator wires.

21. The apparatus of claim 18, wherein when in their respective deployed positions, the first and second pluralities of locator wires respectively define first and second locating perimeters.

22. The apparatus of claim 21, wherein: the first plurality of locator wires is connected to a first tubular member longitudinally mounted for axial movement within the trocar portion between a proximal position corresponding to the retracted position of the first plurality of locator wires, and a distal position corresponding to the deployed position of the first plurality of locator wires; and the second plurality of locator wires is connected to a second tubular member longitudinally mounted for axial movement within the trocar portion between a distal position corresponding to the retracted position of the second plurality of locator wires, and a proximal position corresponding to the deployed position of the second plurality of locator wires.

23. The apparatus of claim 22, wherein the trocar portion includes first and second pluralities of slot-shaped apertures through which the first and second pluralities of locator wires respectively emerge when moved to their respective deployed positions.

24. The apparatus of claim 18, wherein the cutting element is an electrosurgical cutting element and at least some of the first and second plurality of locator wires are electrosurgical electrodes.

25. The apparatus of claim 18, wherein at least one of the locator wires is a hollow wire.

26. The apparatus of claim 18, wherein at least one of the locator wires contains an optical fiber.

27. The apparatus of claim 18, wherein, when in their retracted position, the locator wires of the at least first plurality of locator wires are aligned substantially longitudinally within the trocar portion.

28. Apparatus for localizing a target tissue mass in a body of a patient, comprising:

a tubular trocar portion having a proximal end and a distal end;
an electrosurgical cutting element at the distal end of the trocar portion;
a first wire carrying member longitudinally mounted for axial movement within the trocar portion between a proximal position and a distal position;
a second wire carrying member longitudinally mounted for axial movement within the trocar portion between a proximal position and a distal position;
a first plurality of locator wires attached to the first wire carrying member, wherein the first plurality of locator wires are in a retracted position contained within the trocar portion when the first wire carrying member is in its proximal position, and in a deployed position extending substantially radially from the trocar portion when the first wire carrying member is in its distal position;
a second plurality of locator wires attached to the second wire carrying member, wherein the second plurality of locator wires are in a retracted position contained within the trocar portion when the second wire carrying member is in its distal position, and in a deployed position extending substantially radially from the trocar portion when the second wire carrying member is in its proximal position; a deployment mechanism for moving the first wire carrying member from its proximal position to its distal position and the second wire carrying member from its distal position to its proximal position; and
first and second pluralities of apertures in the trocar portion, corresponding to the first and second pluralities of locator wires, and through which the first and second pluralities of locator wires emerge from the trocar portion when they are moved from their respective retracted positions to their respective deployed positions.

29. The apparatus of claim 28, wherein:
at least some of the locator wires of the first and second plurality of locator wires are electrosurgical electrodes.

30. The apparatus of claim 29, wherein the first and second wire-carrying members are electrically conductive.

31. The apparatus of claim 28, wherein the first wire-carrying member comprises a hollow tubular member, and wherein the second wire-carrying member comprises a second tubular member carried coaxially within the first tubular member.

32. The apparatus of claim 28, wherein the deployment mechanism comprises:
a first slider engageable with the first wire-carrying member and movable between a proximal position and a distal position;
a second slider engageable with the second wire-carrying member and movable between a proximal position and a distal position;
a linking element connecting the first slider to the second slider so that the second slider moves proximally when the first slider moves distally and the second slider moves distally when the first slider moves proximally; and
an actuation element engageable with one of the first and second sliders for moving the one of the sliders between the proximal and distal positions.

33. The apparatus of claim 28, wherein at least some of the first and second pluralities of wires are hollow.

34. The apparatus of claim 28, wherein at least some of the first and second pluralities of wires contain an optical fiber.

35. The apparatus of claim 28, further comprising:

switching means having a first position in which electrical power is provided to the cutting element; and a lock-out mechanism, operable between the switching means and the deployment mechanism, for blocking the movement of the first and second wire-carrying members when the switching means is in its first position.

36. A method of localizing an identified target tissue mass in the body of a patient, the method comprising the steps of:

(a) providing an elongate, tubular trocar having a distal end a proximal end portion, the trocar containing within it a first and second plurality of locator wires that are deployable from the proximal end portion so as to extend substantially radially from the trocar;

(b) inserting the trocar into the body so that its distal end passes through the target tissue mass; and (c) deploying the locator wires substantially radially from the trocar so that the first plurality of locator wires extend into the target tissue mass.

37. The method of claim 36, wherein the trocar contains within it first and second pluralities of locator wires that are deployable from the proximal end portion so as to extend radially from the trocar to respectively define first and second locating perimeters, and wherein the deploying step comprises the step of simultaneously deploying the first and second pluralities of locator wires substantially radially from the trocar, so that the first and second pluralities of locator wires respectively define the first and second locating perimeters.

38. The method of claim 36, wherein the step of inserting the trocar comprises the step of electrosurgically cutting through the target tissue mass.

39. The method of claim 38, wherein the step of deploying the locator wires includes the step of electrosurgically inserting the locator wires into the target tissue mass.

40. The method of claim 39, wherein, following the step of deploying, the method further comprises the step of:

(d) desiccating tissue adjacent the deployed locator wires by supplying the locator wires with electrical energy.

41. The method of claim 36, wherein at least some of the locator wires are hollow wires, and wherein the method further comprises the step of:

(d) during or after the deploying step, injecting a dye through the hollow wires.

42. An elongated device for fixing to a site of target tissue, comprising:

an elongate, tubular shaft having a proximal portion and a distal portion;

a first plurality of locator wires disposed in the distal portion which are movable between a retracted position in which they are contained at least in part within the distal portion of the tubular shaft, and a deployed position in which they extend radially from the distal portion of the tubular shaft distal to their retracted position; and a second plurality of locator wires disposed in the proximal portion of the tubular shaft and movable between a retracted position in which they are contained at least in part within the distal portion of the tubular shaft distal to the retracted position of the first plurality of locator wires, and a deployed position in which they extend radially from the distal portion of the tubular shaft proximal to their retracted position.

43. The elongated device of claim 42 wherein the second plurality of locator wires extend radially a greater distance from the tubular member than the first plurality of locator wires.

* * * * *

UNITED STATES PATENT AND TRADEMARK OFFICE
CERTIFICATE OF CORRECTION

PATENT NO. : 6,312,429 B1
DATED : November 6, 2001
INVENTOR(S) : Fred H. Burbank It is certified that error appears in the above-identified patent and that said Letters Patent is hereby corrected as shown below:

Column 13,
Line 50, "wire carrying" to -- wire-carrying --.

Column 14,
Line 47, change "10" to -- 13 --.
Line 54, change "dessicate" to -- desiccate --.

Column 16,
Lines 5, 8, 11, 14, 17, 20, 22, 25, 27 and 28, change "wire carrying" to -- wire-carrying --.

Signed and Sealed this

Eighth Day of October, 2002

Attest:

Attesting Officer

JAMES E. ROGAN
Director of the United States Patent and Trademark Office